United States Patent [19]

Isaacson et al.

[11] Patent Number: 5,066,300
[45] Date of Patent: Nov. 19, 1991

[54] TWIN REPLACEMENT HEART

[75] Inventors: Milton S. Isaacson, Dayton; Donald E. Holmes, Greenville; Anthony P. Lioi, Dayton, all of Ohio

[73] Assignee: Nu-Tech Industries, Inc., Dayton, Ohio

[21] Appl. No.: 188,906

[22] Filed: May 2, 1988

[51] Int. Cl.⁵ .................................. A61M 1/10
[52] U.S. Cl. ........................... 623/3; 417/413
[58] Field of Search .............. 623/3; 600/16, 17; 417/413, 394, 395

[56] References Cited

U.S. PATENT DOCUMENTS

| | | | |
|---|---|---|---|
| 4,027,215 | 5/1977 | Knight et al. | 318/254 |
| 4,173,796 | 11/1979 | Jarvik | 623/3 |
| 4,238,717 | 12/1980 | Knight et al. | 318/254 |
| 4,277,706 | 7/1981 | Isaacson | 310/80 |
| 4,382,199 | 5/1983 | Isaacson | 310/87 |
| 4,492,903 | 1/1985 | Knight et al. | 318/254 |
| 4,611,578 | 9/1986 | Heimes | 417/383 |

FOREIGN PATENT DOCUMENTS 3323862  1/1985  Fed. Rep. of Germany .......... 623/3

Primary Examiner—David J. Isabella
Assistant Examiner—Stephanie Iantorno
Attorney, Agent, or Firm—Wood, Herron & Evans

[57] ABSTRACT

Two redundant hearts are operated simultaneously for normal patient activity, one of said hearts having sufficient capacity to maintain life at a reduced activity in the event of failure of the other.

A single housing contains two brushless DC motors that pump hydraulic fluid to diaphragms which are part of the two respective hearts. The diaphragms operate, on the blood side, to pump blood in a single blood system connected respectively to the aorta, left atrium, right atrium and pulmonary artery.

If one motor fails, the remaining motor will pump sufficient blood to keep the patient alive until the heart can be replaced.

3 Claims, 3 Drawing Sheets

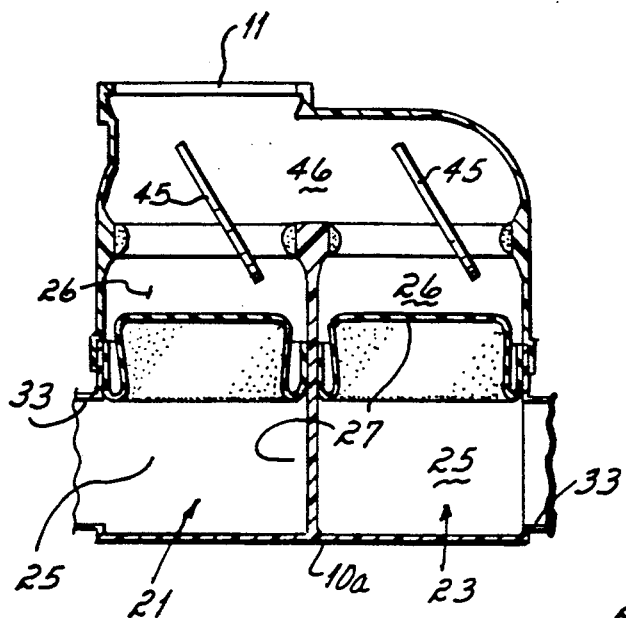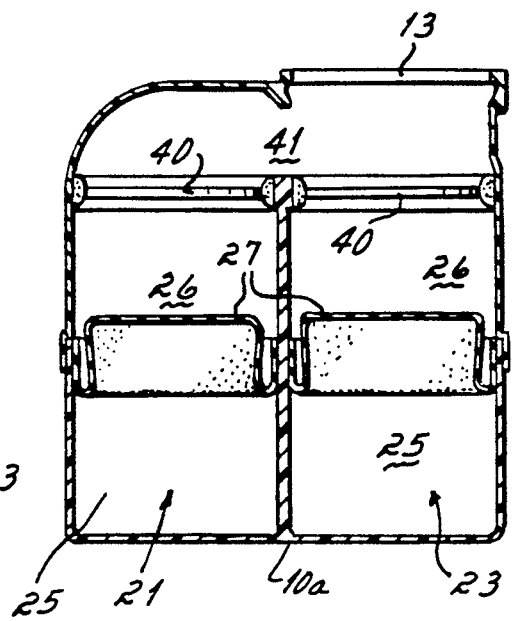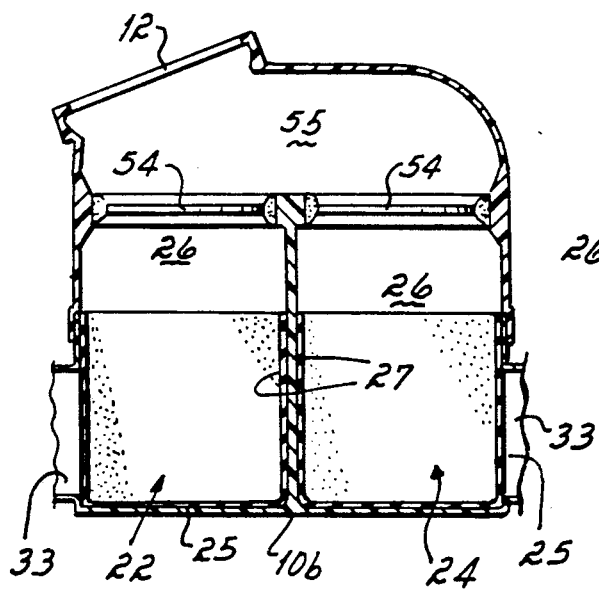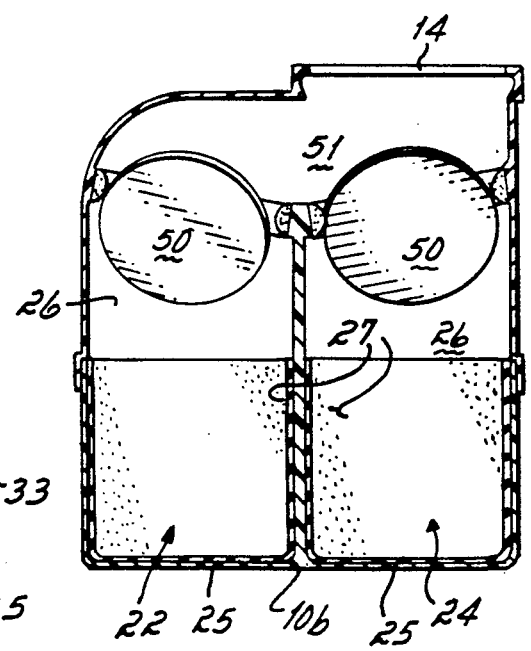

TWIN REPLACEMENT HEART

This invention relates to an artificial or replacement heart of the type described in U.S. Pat. No. 4,173,796. That patent describes a total artificial or replacement heart having a reversible direct current motor and impeller combination operating on a hydraulic fluid confined within the diaphragm system to provide pumping action to blood on the other side of the diaphragms. That heart has not been implanted in a human being although it has promise of being a significantly improved heart over those that have been implanted.

Many people question whether the quality of life of the artificial heart recipient meets human standards and justifies the enormous effort and considerable expense associated with artificial heart implants.

The size and complexity of the artificial heart's drive system is often criticized because of its effect upon patient quality of life. The pneumatic drive system now used with the Jarvik-7 heart is the size of a bookcase and weighs over 320 pounds. The quality of life for a person connected to such a massive and noisy machine which severely restricts movement is clearly not attractive. It is not acceptable for a patient to be permanently tethered to a stationary machine; temporary portability is essential, and permanent portability is highly desirable. One recipient of an artificial heart showed a marked improvement in spirits when he was connected to a portable heart drive system.

Concern over the long term reliability of the artificial heart also impacts upon quality of life. The complexity of both the external drive system and of the internally implanted components causes patients to constantly anticipate heart failure. The first and second recipients of artificial hearts compulsively watched the computer display of the heart beat, as if they needed to monitor the heart's performance.

The artificial heart system must be made much less restrictive and much more reliable if the patient is to enjoy an acceptable quality of life, and if the artificial heart is to gain popular acceptance. Electrically powered total artificial hearts that include an implantable drive system are expected to provide for a much less restrictive life-style. By this elimination of the external drive system, the recipient is only required to carry sufficient power source in order to permit mobility. Unfortunately, in the process of eliminating the external drive system in favor of a small, internal driver, the availability of redundancy in the drive system that was present in the external configuration is lost. The retention of the natural heart in conjunction with an artificial heart implant has been considered as a possible means to retain a backup system for the artificial heart in the event of catastrophic device failure. However, the diseased natural heart's capability as a backup system is highly questionable because the very reason for implanting an artificial heart is the fact that the patient's natural heart is barely able to sustain life and could completely fail at any moment. Furthermore, it can be debated that the implantation of an artificial heart without removing the natural heart is likely to lead to complications stemming from a lack of available space for the artificial heart. Thus, both the use of a total replacement device using current designs and the concept of the natural heart retained as a backup lead to highly questionable reliability due to the absence of a competent backup to the systems. This lack of reliability in present day designs could severely limit the success of the permanent artificial heart.

An objective of the present invention has been to provide a twin heart system to provide in one housing two completely redundant heart systems that will normally operate as a single heart. In the event of failure of one of the heart systems, the other will have sufficient capacity to keep the patient alive although on a reduced level of activity.

It is believed that the redundant heart will enormously enhance the acceptability of the artificial heart to the patient and provide a significantly reduced level of anxiety about the possibility of a failure of the heart system.

Another objective of the invention has been to provide a twin heart system that will take up the space of one heart while providing a 100 cc stroke volume.

These objectives of the present invention are attained by providing a housing having a motor-impeller disposed in a conduit system filled with hydraulic fluid on each side of the housing. The motors are preferably brushless dc reversible motors that act on the hydraulic fluid to cause diaphragms mounted in the housing to move back and forth, thereby pumping blood on the other side of the diaphragms. Two diaphragms on each side of the housing cooperate with inlet and outlet valves to pump blood into the aorta and the pulmonary artery and to receive blood from the left and right atria by providing two heart pumps each half the normal size (50 cc stroke volume) and pumping with the reversing electrohydraulic energy converter (REEC). Normal cardiac output can be provided when they operate concurrently. Since they receive blood from and pump blood into common inlets and outlets, respectively, a space saving is achieved enabling the heart to be smaller and of lesser weight than the Jarvik-7 heart which has been implanted.

One of the most attractive features of the twin or redundant heart is the lessening of anxiety about failure that it permits. The patient is assured that if there is failure of one unit, the remaining unit will continue to function, at a lifesaving level of performance.

The several features and objectives of the present invention will become more readily apparent when viewed in conjunction with the accompanying drawings in which:

FIG. 5 is a cross-sectional view taken on line 5—5 of FIG. 3;

FIG. 6 is a cross-sectional view taken on line 6—6 of FIG. 3;

FIG. 7 is a cross-sectional view taken on line 7—7 of FIG. 3; and

FIG. 8 is a cross-sectional view taken on line 8—8 of FIG. 3.

Figure 1:
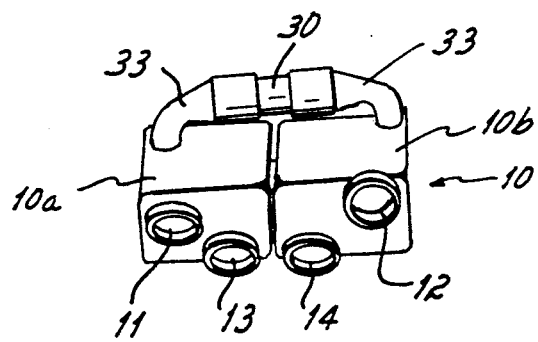
FIG. 1 is a perspective view of the invention.

Referring to FIG. 1, the artificial heart has two housings 10a, 10b, hereinafter referred to as housing 10, and four ports for connection to the two atria, the aorta, and the pulmonary artery. Port 11 is an outlet for connection to the aorta. Port 12 is an outlet for connection to the pulmonary artery. Ports 13 and 14 are inlets connected to the left and right atria that return the blood to the heart.

Figure 2:
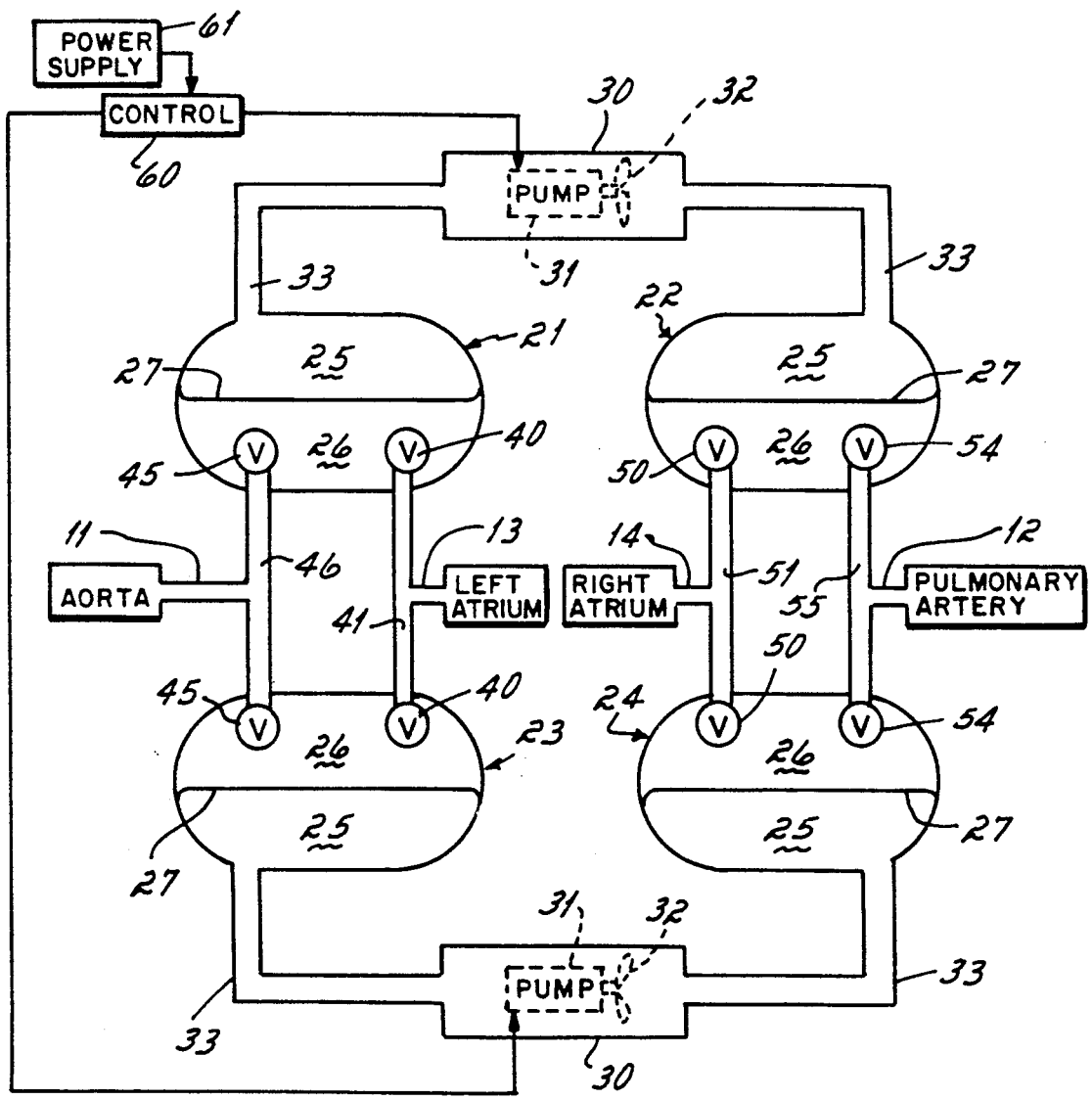
FIG. 2 is a diagrammatic view of the invention.
Figure 3:
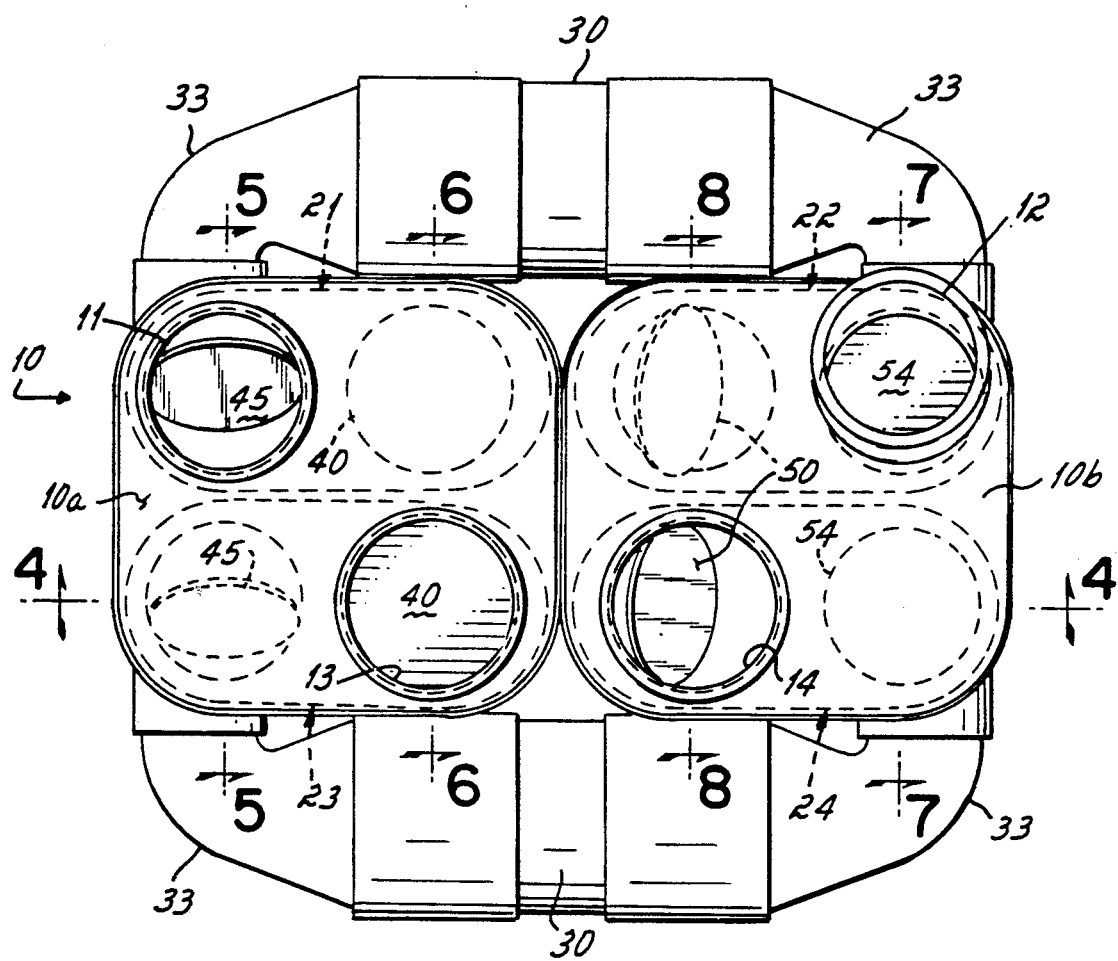
FIG. 3 is a rear view of the invention.
Figure 4:
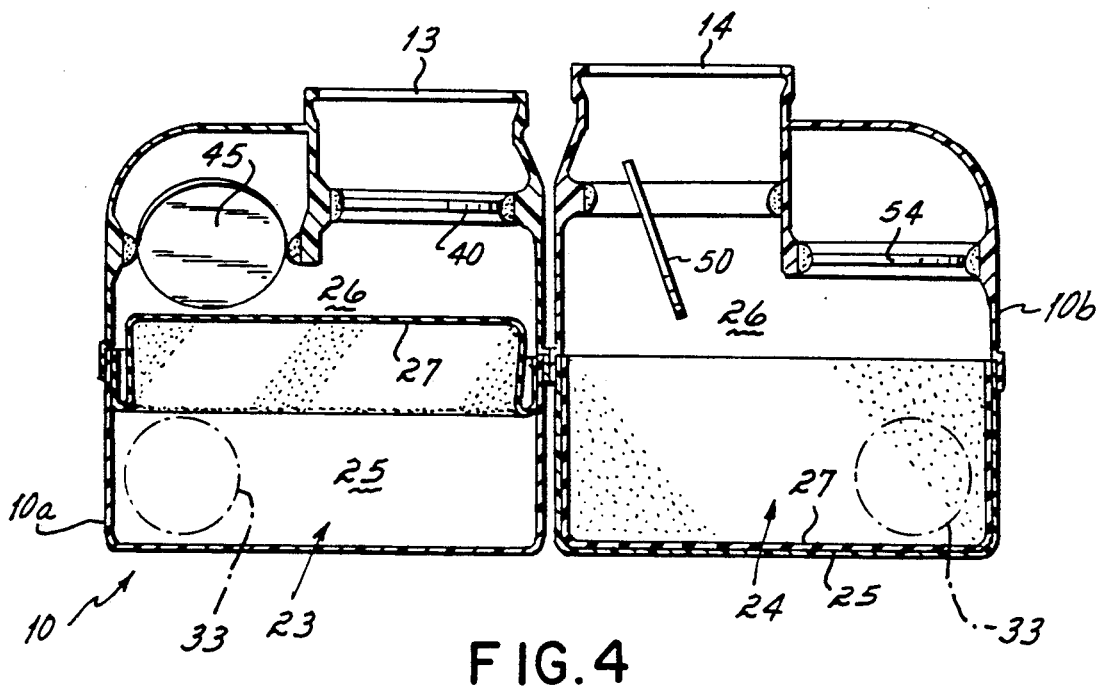
FIG. 4 is a cross-sectional view taken on line 4—4 of FIG. 3.

The housing has four chambers 21, 22, 23, 24. As best seen in FIGS. 2 and 3, each chamber is divided into an outboard pump side 25 and an inboard blood side 26 by a diaphragm 27. Each pair of chambers 21, 22 on the one hand and 23, 24 on the other have a pump 30 consisting of a brushless dc motor 31 and impeller 32 of the type described in U.S. Pat. Nos. 4,277,706, 4,492,903 and 4,027,215. The pump is disposed in a conduit system 33 that is connected to the pump side 25 of the two respective chambers. The conduit system 33 contains a hydraulic fluid that the pump 30 within it moves back and forth to flex the diaphragms 27, thereby causing blood, on opposite sides of the chambers, to flow.

Chambers 21 and 23 are redundant. Each, on the blood side, is connected to prosthetic inlet valves 40 which are in turn connected to a common left atrial compartment 41. The left atrial compartment is connected to the inlet port 13. The chambers 21 and 23 are also connected to prosthetic outlet valves 45 that communicate with an aortic compartment 46 which in turn is connected to the aortic port 11. The blood side 26 of the chambers 21 and 23, combined with the flexing diaphragms 27, perform the function of the left ventricle of a normal heart.

On the other side of the housing the chambers 22 and 24 are redundant. The blood side of those chambers is connected to prosthetic inlet valves 50 which communicate to a common right atrial compartment 51. The right atrial compartment 51 is connected to the right atrial port 14. The other side of the chambers 22, 24 are connected to prosthetic outlet valves 54 which connect to a pulmonary arterial compartment 55 connected to the pulmonary arterial port 12.

The motors are connected to a common control system 60 and power supply 61. The power supply 61 may be implanted, but accessible from outside the body, which is the subject of our copending application Ser. No. 172,654, filed Mar. 24, 1988. The pump and control system generally are of the type disclosed in U.S. Pat. No. 4,173,796 with the control system being disclosed more specifically in U.S. Pat. Nos. 4,027,215 and 4,238,717.

In the operation of the invention, the two pumps 30 are normally operated simultaneously in a reversing mode in a range from approximately 70 to 120 beats per minute. This causes the diaphragm 27 on two chambers 21, 23 to simultaneously drive blood through the aorta while in the opposite chambers 22, 24 blood is drawn into the chambers 22, 24 through the right atrium. Upon reversal, blood is drawn into chambers 21 and 23 through the left atrium while blood is pumped out of the chambers 22 and 24 into the pulmonary artery. If there should be a failure of one of the two pumps, the remaining pump will continue to operate causing a flow of blood throughout the circulatory system but at one-half the normal stroke volume and at a faster heart rate. If it is a 100 cc stroke volume, then in the failure of one pump the blood pumped will be reduced to half that level or 50 cc per stroke volume. Thus, the patient remains alive until the heart can be replaced.

From the above disclosure of the general principles of the present invention and the preceding detailed description of a preferred embodiment, those skilled in the art will readily comprehend the various modifications to which the present invention is susceptible. Therefore, we desire to be limited only by the scope of the following claims and equivalents thereof:

We claim:

1. A replacement heart comprising:
a housing having left and right atrial inlets and left and right ventricular outlets,
means dividing said housing into two sets of two chambers, diaphragms dividing each chamber into a blood side and a pump side,
one chamber of each set connected on its blood side to said left atrial inlet and said left ventricular outlet,
the other chamber of each set connected on its blood side to said right atrial inlet and right ventricular outlet,
each set of chambers having a pump housing and a reversible dc motor and impeller in each housing, conduit connecting said housing to the pump side of each said chamber in each set,
a hydraulic fluid in said pump housing, conduit and pump side of each set,
and a control system including a power supply for simultaneously operating said motors and reversing them at a rate corresponding to the rate needed to sustain a patient's activity.

2. A twin replacement heart comprising:
a housing having two identical artificial heart systems connected to one pair of outlets and one pair of inlets,
each heart system including a reversible brushless dc motor and impeller forming a pump,
and a power supply and control system for simultaneously operating said motors and reversing them at a rate suitable to a patient's needs,
one of said motors and pump having sufficient capacity to supply a patient's needs, on a reduced level, in the event of the failure of the other motor and pump.

3. A replacement heart comprising:
a central housing divided into two chambers on one side and two chambers on the other side,
a diaphragm across each chamber dividing the chamber into an outboard pump side and an inboard blood side,
a pump conduit on each side of said housing connected to the pump side of each chamber,
a reversible brushless dc motor and pump disposed in said pump conduit,
the blood sides of opposed chambers across said housing being connected to two respective inlets and two respective outlets,
whereby the inboard blood sides of the chambers function as a single replacement heart and the outboard pump sides and pumps function as a redundant drive system for said single replacement heart.

* * * * *